United States Patent
Chen et al.

(10) Patent No.: US 8,367,104 B2
(45) Date of Patent: Feb. 5, 2013

(54) FAST DISSOLVING/DISINTEGRATING COATING COMPOSITIONS

(75) Inventors: Jen-Chi Chen, Morrisville, PA (US); Frank J. Bunick, Randolph, NJ (US); Gerard McNally, Berwyn, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 30 days.

(21) Appl. No.: 12/913,855

(22) Filed: Oct. 28, 2010

(65) Prior Publication Data

US 2011/0097399 A1 Apr. 28, 2011

Related U.S. Application Data

(60) Provisional application No. 61/255,626, filed on Oct. 28, 2009.

(51) Int. Cl.
*A61K 9/48* (2006.01)
*A61K 9/68* (2006.01)
*A61K 9/28* (2006.01)
*A61K 9/30* (2006.01)

(52) U.S. Cl. ......... 424/463; 424/440; 424/474; 424/475

(58) Field of Classification Search ................. None
See application file for complete search history.

(56) References Cited

U.S. PATENT DOCUMENTS

| | | | |
|---|---|---|---|
| 4,965,072 A | 10/1990 | Alexander et al. | |
| 5,807,580 A | 9/1998 | Luber | |
| 6,413,549 B2 | 7/2002 | Green et al. | |
| 6,627,224 B2 | 9/2003 | Colonno et al. | |
| 6,660,382 B2 | 12/2003 | Nouri et al. | |
| 7,125,562 B2 | 10/2006 | Daggy et al. | |
| 2002/0068088 A1* | 6/2002 | Gruber | 424/490 |
| 2005/0042277 A1* | 2/2005 | Srinivas et al. | 424/452 |
| 2005/0255054 A1 | 11/2005 | Phlilp, Jr. et al. | |
| 2006/0003007 A1 | 1/2006 | Odidi et al. | |
| 2006/0188570 A1 | 8/2006 | Batra et al. | |
| 2007/0077300 A1 | 4/2007 | Wynn et al. | |
| 2008/0292669 A1 | 11/2008 | Deng et al. | |
| 2009/0047330 A1 | 2/2009 | Bangalore | |

FOREIGN PATENT DOCUMENTS

| | | |
|---|---|---|
| EP | 0878189 B1 | 2/2005 |
| WO | WO 99/47125 A1 | 9/1999 |
| WO | WO 2007/103286 A2 | 9/2007 |
| WO | WO 2008079963 A2 | 7/2008 |

OTHER PUBLICATIONS

US Patent Documents—None.*
Non-Patent Documents—None.*
International Search Report for PCT/US2010/054431 dated Sep. 12, 2011.
S. C. Porter, *Coating of Pharmaceutical Dosage Forms*, Remington's Pharmaceutical Sciences, 18th Ed. Chapter 90, 1990, p. 1666-1675.
Price, J., *Coating of Pharmaceutical Dosage Forms*, Remington's Pharmaceutical Sciences, 15th Ed., 1975, p. 1613.

* cited by examiner

*Primary Examiner* — Robert A Wax
*Assistant Examiner* — Jeffrey T Palenik
(74) *Attorney, Agent, or Firm* — Laura A. Donnelly

(57) ABSTRACT

A pharmaceutical composition for oral administration comprising a core and a film coating on the core that exhibits enhanced disintegration characteristics is disclosed. The film coating comprises a film forming polymer, an organic solvent, a super-disintegrant and, optionally, an acid labile material.

11 Claims, No Drawings

FAST DISSOLVING/DISINTEGRATING COATING COMPOSITIONS

This application claims priority from U.S. Provisional Applications Ser. No. 61/255,626 filed Oct. 28, 2009, the contents of each of which are hereby incorporated by reference in their entirety.

FIELD OF THE INVENTION

The present invention relates to pharmaceutical compositions and more particularly film coated tablet compositions having enhanced disintegration characteristics. The film coated tablet composition is coated with a solvent-based film coating composition that contains a polymer that is soluble in water and in polar organic solvents, a super-disintegrant, and optionally an acid labile material.

BACKGROUND OF THE INVENTION

Standard therapy in the treatment of many illnesses is the administration of a pharmaceutically active ingredient in tablet dosage form, which often requires the patient to swallow the tablet intact. In order to improve the swallowability of a tablet, it is known in the art to coat the surface of the tablet with a polymeric film, which provides several benefits to the patient. First, it reduces the adhesion of the tablet to the inner surface of the mouth, thereby increasing the patient's ability to swallow the tablet. Second, it aids in masking the unpleasant taste for certain drugs. It also can protect components from atmospheric degradation and improve appearance.

Polymeric films typically used in such film coating include, for example, (1) vinyl polymers such as polyvinylpyrrolidone, polyvinyl alcohol and acetate, (2) cellulosics such as methyl and ethyl cellulose, hydroxyethyl cellulose, hydroxypropyl methylcellulose and hydroxypropylcellulose, (3) acrylates and methacrylates, (4) copolymers such as vinyl-maleic acid and styrene-maleic acid, and (5) natural gums and resins such as zein, gelatin, shellac and acacia. See Remington's Pharmaceutical Sciences, 15th Ed. Mack Publishers (1975) p. 1613.

While the film coating adds certain advantages to the tablet formulations, one disadvantage is that the film coating may reduce the onset of action of the drug by retarding disintegration of the tablet. In certain cases, this can retard the disintegration of the tablet within the first few minutes of contact with a liquid medium. This can affect the performance of certain medications such as antacids where a fast onset of action is desirable. There is thus a need for a film coating composition which exhibits enhanced disintegration characteristics in order to provide more rapid delivery of active and faster onset of action.

The use of disintegrating agents such as dried starch, sodium alginate, lactose, sodium bicarbonate, calcium carbonate, polyvinyl pyrrolidone, microcrystalline cellulose and the like in the tablet core or granulation mixture of a swallowable tablet formulation is known. For example, U.S. Pat. No. 4,965,072 discloses the use of a mixture of magnesium sulphate heptahydrate and sodium hexametaphosphate to prepare a granulating composition with an active ingredient, which, when formulated into a swallowable tablet, exhibits rapid disintegration or dispersion.

In recent years, several newer agents have been developed known as "super-disintegrants". These newer substances are more effective at lower concentrations with greater disintegrating efficiency and mechanical strength. On contact with water the super-disintegrants swell, hydrate, change volume or form and produce a disruptive change in the tablet. Effective super-disintegrants provide improved compressibility, compatibility and have no negative impact on the mechanical strength of formulations containing high-dose drugs. However, the use of disintegrating agents and/or super-disintegrants in the tablet core in such a manner does not address the problem associated with the slow dissolution of the polymeric film in a film coated tablet.

U.S. Pat. No. 6,413,549 to R. P. Sheerer Corporation discloses a rapidly disintegrating, freeze-dried dosage form comprising coarse particles of active coated with a polymer or lipid material.

U.S. Pat. No. 7,125,562 to SmithKline Beecham Corporation discloses disintegrating methylcellulose tablets. The patent discloses that the tablets have a first phase and a second phase blended with the first phase and that each phase may contain a disintegrant and a polymer.

European Patent No. EP878189 B1 to Hercules Incorporated discloses the use of hydrophobically modified polysaccharides, including hydroxypropylcellulose, in personal care products.

U.S. Application No. 20050255054 to Philip et al. discloses a dissolvable tooth whitening strip that contains a dissolvable substance such as a freeze-dried hydrogel containing acemannan.

U.S. Application No. 20070077300 A1 to Wynn et al. discloses oral dosage forms that contain salivation inducing agents that may be in the core and/or the coating of the dosage form.

U.S. Application No. 20080292669 to SmithKline Beecham Corporation discloses foamed substrates for transmucosal and/or transdermal applications that comprise one or more polymers and one or more foaming agents, and that may comprise one or more plasticizers, hydrophobic barrier agents, tooth whitening agents, antioxidants, preservatives, super-disintegrants or absorbents, flavorants, deodorants, breath freshening agents, colorants, surfactants, film modifiers, cross-linking agents, antimicrobial agents, control release agents, other therapeutic agents, or any combinations thereof.

International Application No. WO2008079963 to Cambrex Charles City, Inc. discloses ionic complexes of anion-containing APIs that can be coated with a pharmaceutically acceptable coating.

U.S. Application No. 20090047330 A1 to Bangalore discloses water soluble polymer based edible films that are prepared using the formulation composition disclosed therein along with other ingredients including plasticizers, fillers, taste masking agents, disintegrants, and colorants.

U.S. Pat. No. 6,627,224 to Bristol-Myers Squibb Co. discloses a process for making a pharmaceutical composition that comprises entecavir, comprising forming a solution of entecavir and an adhesive in a solvent, depositing the solution on substrate particles, drying and mixing the coated substrate particles with other ingredients, including disintegrants.

U.S. Pat. No. 6,660,382 to Ethypharm discloses a process for preparing coated granules with masked taste and immediate release of active that comprises: dry-mixing the constituents of a powder comprising at least the active and a disintegrant; granulating the resultant powder in the presence of a binder to obtain granules; coating the granules formed by spraying a suspension comprising at least one coating agent and one disintegrant; and drying the resulting coated granules.

U.S. Pat. No. 5,807,580 to McNeil PPC, Inc. discloses pharmaceutical compositions comprising a film coated tablet exhibiting enhanced disintegration characteristics that comprises a hydrophilic film forming polymer and an alkaline agent such as an alkali metal, an alkali earth metal carbonate, or a bicarbonate such as sodium or potassium bicarbonate, wherein the alkaline agent reduces the disintegration time of the film coating by increasing the rate of removal of the film coating polymers.

There continues to be a need for pharmaceutical compositions and more particularly film coated tablet compositions having enhanced disintegration characteristics

SUMMARY OF THE INVENTION

Immediate release film coatings on tablets inherently have a rate limiting step since the polymer must hydrate to an extent before they dissolve, even if they are water soluble. Most films cannot support the addition of materials which may aid in this disintegration, since those materials would not be compatible with an aqueous based coating solution, or in the case of a film strip dosage form, a casting solution comprising an active ingredient.

The pharmaceutical composition of the invention, which comprises a core and a film coating comprising a film forming polymer, a polar organic solvent, a super-disintegrant, and, optionally, an acid labile material, on the core, exhibits enhanced disintegration characteristics. The polymer, which is both soluble in a polar organic solvent and in water is selected in order to suspend the super-disintegrant intact prior to application (e.g., spraying, dipping or casting as a film). Typical aqueous coating systems would deactivate the super-disintegrant during processing, or would swell to the point in which they could not be applied since the size would be too large. The organic solvent system allows them to retain their swelling properties in the finished coating. The novel coating composition can produce fast dissolving/disintegrating films. The super-disintegrants are substantially intact throughout the coating process.

The super-disintegrant reduces the disintegration time of the film coating by increasing the rate of removal of the film coating polymers, through swelling and disintegration of the film. The acid labile material will enhance the rate of film disintegration. When the film coated tablet contacts a liquid medium, it immediately reacts with the liquid medium to disintegrate the film coating.

Preferably, the film forming polymer is hydroxypropylcellulose.

Preferably, the polar organic solvent is selected from ethanol, acetone, methanol and isopropanol. In one embodiment, the polar organic solvent is a mixture of two or more organic solvents. In one embodiment the organic solvent is a mixture of ethanol and a secondary solvent selected from acetone, methanol and isopropanol, wherein the ratio of ethanol to secondary solvent is from about 50:50 to about 99:1.

Preferably, the super-disintegrant is selected from low substituted hydroxypropyl cellulose (L-HPC), sodium starch glycolate, sodium croscarmellose, cross-linked polyvinylpyrrolidone; soy polysaccharide; cross-linked alginic acid; gellan gum; xanthan gum; calcium silicate; and ion exchange resin. In one preferred embodiment the super-disintegrant is croscarmellose sodium, since it is ionic. The ionic property of croscarmellose sodium is especially advantageous in the preparation and storage of an ethanol based coating solution or suspension, since this property inhibits the reaction or swelling of the super-disintegrant in the solution or suspension. In another preferred embodiment, the super-disintegrant is L-HPC.

Preferably, the acid labile material is selected from sodium bicarbonate, potassium bicarbonate, sodium carbonate and sodium glycine carbonate.

DETAILED DESCRIPTION OF THE INVENTION

In accordance with the present invention, the film coating is formed on at least a portion, preferably on all, of the exposed surface of the core containing the pharmaceutical actives. The film coating may optionally contain a plasticizer, such as castor oil, triethylcitrate, tributyl citrate, triacetin, mineral oil, polyethylene glycol, propylene glycol or glycerine; a coloring or an opacifying agent, such as titanium dioxide; a flavoring agent; a sensate, such as a cooling agent, a warming agent or a tingling agent; and/or a sweetening agent to improve palatability. The film coating will generally contain (w/w) about 1 to about 20 percent of the film forming polymer.

The film coating is applied to standard tablet or caplet cores containing the active ingredient(s). The cores are prepared in accordance with standard pharmaceutical tableting techniques, including wet-granulation, dry-granulation, direct compression, spheronization and the like. The coating is applied to the cores using conventional pharmaceutical coating equipment, such as an Accela-Cota™ coating pan from Thomas Engineering, Inc., Hoffman Estates, Ill. or fluidized bed coating equipment such as a Wurster coating unit. Other film coating techniques suitable for use in the present invention are described in Remington's Pharmaceutical Sciences (edited by A. L. Gennaro), Mack Publishing Co., Easton, Pa., 18th ed., Chapter 90 (1990), which is hereby incorporated by reference. The preferred method for applying the film coatings of the present invention is spray coating using conventional coating equipment but fluid-bed coating may also be employed.

The film coating (dried) generally constitutes from about 1 to about 10, preferably about 2 to about 6, and more preferably about 2 to about 4, percent by weight of the total weight of the solid dosage form. In one embodiment the thickness of the dried film coating is from about 30 microns to about 60 microns. With regard to chewable tablets, more preferably, the film coating (dried) constitutes from about 0.2 to about 10 percent, by weight of the total weight of the solid dosage form. Also with regard to chewable tablets, more preferably, the thickness of the dried film coating is from about 2 to about 40 microns.

The film coatings of the present invention may be employed for the coating of a variety of actives where a quick onset of action is desirable. The preferred pharmaceutical tablets with which the film coatings of the present invention are used contain an antacid where an immediate release of the active ingredient in the stomach is desirable to neutralize stomach acid and provide immediate relief from acid indigestion, heartburn and the like. Typical antacids are made from a variety of inorganic salts such as calcium carbonate, sodium bicarbonate, magnesium salts and aluminum salts. Magnesium hydroxide and aluminum hydroxide are the most potent magnesium and aluminum salts and are often used in combination. In addition, magnesium oxide, magnesium carbonate, aluminum phosphate, magaldrate, magnesium trisilicate, and aluminum sucrose sulfate (sucralfate) may also be employed with the present invention. In a preferred embodiment, the antacid is selected from a combination of calcium carbonate and magnesium carbonate or calcium carbonate and magnesium hydroxide. The amount of antacid in the preparation may conveniently be, for example, in the range of 10%-90% w/v of the composition. Advantageously, an H2 receptor blocking agent such as famotidine, ranitidine and/or cimetidine may also be combined with the antacid, or the film coating can be applied to the H2 receptor blocking dose. Other active ingredients for which the coatings of the present invention are suitable include antiflatulents, anti-inflammatory agents, analgesics, anti-diarrheals and combinations thereof.

As used herein, the term "dosage form" applies to any solid object, semi-solid, or liquid-filled composition designed to contain a specific pre-determined amount (dose) of a certain ingredient, for example, an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

Suitable "active ingredients" for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine. A preferred gastrointestinal agent is omeprazole.

In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient is selected from analgesics, anti-inflammatories, and antipyretics, e.g., non-steroidal anti-inflammatory drugs (NSAIDs), including propionic acid derivatives, e.g., ibuprofen, naproxen, ketoprofen and the like; acetic acid derivatives, e.g., indomethacin, diclofenac, sulindac, tolmetin, and the like; fenamic acid derivatives, e.g., mefanamic acid, meclofenamic acid, flufenamic acid, and the like; biphenylcarbodylic acid derivatives, e.g., diflunisal, flufenisal, and the like; and oxicams, e.g., piroxicam, sudoxicam, isoxicam, meloxicam, and the like. In one particular embodiment, the active ingredient is selected from propionic acid derivative NSAID, e.g., ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another particular embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof. A preferred (analgesic) is acetaminophen.

In another embodiment of the invention, the active ingredient may be selected from upper respiratory agents, such as pseudoephedrine, phenylephrine, guaifensin, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. Typically, the dosage form comprises at least about 1 weight percent, for example, the dosage form comprises at least about 5 weight percent, say at least about 20 weight percent, of a combination of one or more active ingredients. In one embodiment, a core comprises a total of at least about 25 weight percent (based on the weight of the core) of one or more active ingredients.

The active ingredient or ingredients may be present in the dosage form in any form.

Each core may be any solid form. As used herein, "core" refers to a material which is at least partially enveloped or surrounded by another material and has a thickness of at least about 2 mm to about 30 mm. Preferably, a core is a self-contained unitary object, such as a tablet or capsule. Typically, a core comprises a solid, for example, a core may be a compressed or molded tablet or a hard or soft capsule.

In one embodiment the core is a tablet capable of being chewed (i.e., a chewable tablet) or capable of disintegrating in the oral cavity. In one embodiment, the tablet is designed to disintegrate in the mouth when placed on the tongue in less than about 60 seconds, e.g., less than about 45 seconds, e.g., less than about 30 seconds, e.g., less than about 15 seconds. The coating film of the present invention would be especially advantageous as a coating for a chewable or orally disintegrating tablet since it disintegrates sufficiently quickly to allow the core to be chewed or similarly disintegrate. Other types of coatings disintegrate slowly such that the dosage form may be inadvertently swallowed, or leave an unpalatable film or film shards in the mouth.

In one embodiment, the tablet meets the criteria for Orally Disintegrating Tablets (ODTs) as defined by the draft Food and Drug Administration guidance, as published in April, 2007. In one embodiment, the tablet meets a two-fold definition for orally disintegrating tablets including the following criteria: 1) that the solid tablet is one which contains medicinal substances and which disintegrates rapidly, usually within a matter of seconds, when placed upon the tongue and 2) be considered a solid oral preparation that disintegrates rapidly in the oral cavity, with an in vitro disintegration time of approximately 30 seconds or less, when based on the United States Pharmacopeia (USP) disintegration test method for the specific medicinal substance or substances.

The cores may be prepared by any suitable method, including for example compression or molding, and depending on the method by which they are made, typically comprise active ingredient and a variety of excipients.

In one embodiment of the invention the dosage form is applied as a subcoating and is further coated or partially coated with a gelatinous coating. In one embodiment the subcoating comprises openings which expose the core, and further enhance the disintegration of the dosage form. The gelatinous coating may be applied by a variety of methods including dipping, molding, or enrobing and may comprise a coating material such as gelatin, gellan gum, starch, hypromellose or modified starch and a thickening agent such as carrageenan and xanthan gum. In one embodiment the openings in the sub-coating are produced using a laser.

In one embodiment the coating solution or suspension is substantially free of water. As used herein, substantially free is defined as less than 0.5 percent, such as less than 0.2 percent of water. In one embodiment the film strip solution or suspension is substantially free of water. As used herein, substantially free is defined as less than 0.5 percent, such as less than 0.2 percent of water.

When an active ingredient is incorporated into the film as a dosage form, it may be present in the dosage form in any form. For example, the active ingredient may be dispersed at the molecular level, e.g., melted or dissolved, within the dosage form, or may be in the form of particles, which in turn may be coated or uncoated. If the active ingredient is in form of particles, the particles (whether coated or uncoated) typically have an average particle size of about 1 micron to about 2000 microns. In one embodiment, such particles are crystals having an average particle size of about 1 micron to about 300 microns. In yet another embodiment, the particles are granules or pellets having an average particle size of about 50 microns to about 2000 microns, e.g., from about 50 microns to about 1000 microns or from about 100 microns to about 800 microns. In another embodiment the coating of the present invention comprises a colorant, which may include a lake, a dye, or an opacifier such as titanium dioxide or mixtures thereof.

Specific embodiments of the present invention are illustrated by way of the following examples. This invention is not confined to the specific limitations set forth in these examples, but rather to the scope of the appended claims. Unless otherwise stated, the percentages and ratios disclosed herein are by weight.

EXAMPLES

The polymer (e.g., polyvinyl alcohol, polyvinyl pyrrolidone, copolymer of vinyl pyrrolidone and vinyl acetate, hydroxypropyl cellulose and Eudragit E100) is dissolved in organic solvent (e.g., alcohols, ketones, esters, and halogenated hydrocarbon). The super-disintegrant (e.g., low substituted hydroxypropylcellulose (L-HPC), sodium starch glycolate, sodium croscarmellose) is then dispersed in the resulting polymer solution. The acid labile material (e.g., sodium carbonate, sodium bicarbonate, sodium glycine carbonate), if employed, is also dispersed in the resulting polymer solution.

The coating composition can be applied onto tablets, capsules, or caplets by a spraying or a dipping method. The coating system dries as a polymer film, and provides the bulk needed to create a distinct fast dissolving/disintegrating shell on substrates.

Composition:
A. A film-forming composition comprising about 5-15% solids in absolute ethanol, with:
  Water-soluble polymer, such as HPC (about 2-8% total solution)
  Super-disintegrant, such as L-HPC (about 3-10% total solution)
  Optional acid labile materials, such as sodium bicarbonate (about 0-5% total solution)
  Optional plasticizers, such as PEG 400 (about 0-4% total solution)
B. A dosage form having a rapidly disintegrating coating comprising:
  Water-soluble polymer (about 15-40%)
  Super-disintegrant, such as sodium croscarmellose (about 50-75%)
  Optional acid labile materials, such as sodium carbonate (about 0-30%)
  Optional plasticizers, such as PEG-400 (about 0-25%)
  (advantageously, the coating disintegrates promptly upon exposure to GI fluids, avoiding a lag-time for dissolution of the active ingredient).

Process Options:
The coating compositions work well in spraying and dipping applications.

EXAMPLES

Example 1

Fast Dissolve HPC Film Coating

Preparation of Coating Solution Comprising HPC and Super-Disintegrant
1) 5.75 g of hyroxypropylcellulose (HPC, commercially available as Klucel EF from the Ashland Corporation in Covington, Ky.) is mixed into 207 g of absolute ethyl alcohol with overhead mixer at room temperature to make 2.7% solids of HPC solution.
2) 17.25 g of sodium croscarmellose (a super-disintegrant commercially available from the FMC Corporation in Philadelphia, Pa. as Ac-Di-Sol) is then added into the HPC solution with agitation at room temperature to make 10% solids of HPC/sodium croscarmellose suspension.

Film Coating of Tablet Cores

Commercially available Tylenol® Extra Strength uncoated caplets (900 g) are charged to a 12-inch vented coating pan (commercially available from the O'Hara Technologies in Richmond Hill, ON, Canada). The batch is spray coated with a spray rate of approximately 10 grams per minute, a pan speed of about 10 RPM, an inlet air temperature of about 56° C., and an atomization air pressure of about 25 psi. 115 grams of the coating suspension are sprayed, which are equivalent to 23 g of dried coating, or about a 2.5% weight gain.

The coated tablets are placed into a vessel containing 900 mL of purified water, wherein the coating disintegrates in less than 15 seconds. The coating on many commercially available coated tablets would take minutes to disintegrate.

Example 2

Fast Dissolve HPC Film Based Form

Preparation of Film Casting Solution Comprising HPC and Super-Disintegrant
The orally dissolving film based dosage form is prepared according to Table 1.
1) 13.78 g of HPC is mixed into 261.8 g of absolute ethyl alcohol with an overhead laboratory mixer at room temperature to make 5% solids of HPC solution at 20 RPM for 20 minutes.
2) Sucralose, potassium sorbate, raspberry flavor and phenylephrine HCl are added to the mixture above.
3) Sodium croscarmellose and the remaining ethanol are then added into the HPC solution while mixing at 20 RPM at room temperature to make 15% solids suspension.

TABLE 1

Orally Dissolving Film Formulation

| Material | Mg/Solution | mg/dried film | %/dried film |
|---|---|---|---|
| Hydroxypropylcellulose | 13.78 | 13.78 | 21.200 |
| Sodium Croscarmellose | 41.33 | 41.33 | 63.585 |
| Phenylephrine | 7.50 | 7.50 | 11.539 |
| Sucralose | 1.50 | 1.50 | 2.308 |
| Raspberry Flavor | 0.80 | 0.80 | 1.231 |
| Potassium Sorbate | 0.09 | 0.09 | 0.139 |
| Ethanol | 152.0 | NA* | NA* |
| TOTAL | 217.0 | 65.00 | 100.00 |

*remove upon drying

Film Strips Preparation
1) Approximately 217.0 mg of the suspension is poured to a glass plate with edges.
2) The mixture is then dried at room temperature for 5-6 hours until the surface is dry.
3) The sample is removed from the glass plate.

Example 3

Comparative Example of Hydroxypropylcellulose Film without a Disintegrant 1) 6.00 g of hydroxypropylcellulose (HPC, commercially available as Klucel EF from the Ashland Corporation in Covington, Ky.) is mixed into 94 g of absolute ethyl alcohol with overhead mixer at room temperature to make 6% solids of HPC solution.
2) Approximately 2 grams of the solution in (1) is cast into a film of approximately 1 mm and allowed to dry at 40° C. for 1 hour.
3) Approximately 2 grams of the solution prepared in Example 1 (comprising the super-disintegrant) is cast into film of approximately 6.5 mm, 5 mm and 3.5 mm, and allowed to dry at 40° C. for 1 hour.

4) The films comprising a super-disintegrant and those without a super-disintegrant were mounted onto an enhancer cell device and placed in the center of a 400 ml beaker. 250 mL of purified water at 25° C. was poured into the beaker to contact the film surface. The disintegration time was recorded accordingly. The HPC films comprising the super-disintegrant (prepared according to Example 1) disintegrated in 11 seconds, 6 second and 3 seconds, respectively, for the 6.5 mills, 5 mills and 3.5 mills films. The HPC film (1 mill) prepared without the super-disintegrant disintegrated in greater than 4 minutes. This is unexpected since the film without the super-disintegrant was thinner than the corresponding films with the super-disintegrant, and thinner films generally disintegrate at a faster rate.

Although only preferred embodiments of the invention are specifically described above, it will be appreciated that modifications and variations of the invention are possible without departing from the spirit and intended scope of the invention.

The invention claimed is:

1. A pharmaceutical dosage form having enhanced disintegration characteristics comprising a core, wherein the core is selected from the group consisting of a tablet and a caplet, and a film coating, wherein the film coating consists of hydroxypropylcellulose and sodium croscarmellose, wherein the film coating weight gain is about 2.5%, and wherein the film coating disintegrates in water in less than 15 seconds.

2. The pharmaceutical dosage form of claim 1, further comprising openings which extend through a surface of the film coating to a surface of the core.

3. The pharmaceutical dosage form of claim 1, wherein the tablet is selected from a chewable tablet and an orally disintegrating tablet.

4. A method of preparing a pharmaceutical dosage form, comprising preparing a film coating; and applying the film coating to a core, wherein preparing the film coating comprises a step of suspending a super-disintegrant in an organic solvent and a step of dissolving the hydroxypropylcellulose in the organic solvent.

5. The method of claim 4, wherein the organic solvent is selected from the group consisting of ethanol, acetone, methanol and isopropanol.

6. The method of claim 4, wherein the organic solvent is a mixture of two or more organic solvents.

7. The method of claim 6, wherein the organic solvent is a mixture of ethanol and a secondary solvent selected from acetone, methanol and isopropanol.

8. The method of claim 7, wherein the ratio of ethanol to secondary solvent is from about 50:50 to about 99:1.

9. The method of claim 4, wherein the film coating is applied to the core via a spraying process.

10. The pharmaceutical dosage form of claim 1, wherein the film coating is prepared by suspending the hydroxypropylcellulose and the croscarmellose in an organic solvent.

11. The pharmaceutical dosage form of claim 1, wherein the core comprises acetaminophen.

* * * * *